United States Patent [19]
Zygourakis et al.

[11] Patent Number: 5,487,112
[45] Date of Patent: Jan. 23, 1996

[54] METHOD AND APPARATUS FOR TIME-RESOLVED MEASUREMENTS OF LYMPHOCYTE FUNCTION AND AGGREGATE STRUCTURE USING COMPUTER-AUTOMATED MICROSCOPY

[75] Inventors: Kyriacos Zygourakis; John L. Bednarczyk; Bradley W. McIntyre; Michael W. Glacken, all of Houston, Tex.

[73] Assignee: Board of Regents, The University of Texas System, Austin, Tex.

[21] Appl. No.: 483,038

[22] Filed: Feb. 20, 1990

[51] Int. Cl.⁶ ............................ G06K 9/00; G06F 15/00; G01N 33/48
[52] U.S. Cl. ............................ 382/6; 364/413.08; 356/39
[58] Field of Search .................. 382/6; 364/413.08, 364/413.13, 555; 377/11; 356/39, 335, 336; 422/73

[56] References Cited

U.S. PATENT DOCUMENTS

| | | | |
|---|---|---|---|
| 3,989,382 | 11/1976 | Kent et al. | 356/39 |
| 4,135,819 | 1/1979 | Schmid-Schonbein | 356/39 |
| 4,197,088 | 4/1980 | Meserol et al. | 422/73 |
| 4,295,200 | 10/1981 | Johnson | 364/555 |
| 4,501,491 | 2/1985 | Brede et al. | 356/39 |
| 4,580,895 | 4/1986 | Portel | 422/73 |
| 4,773,097 | 9/1988 | Suzaki et al. | 382/6 |
| 4,786,813 | 11/1988 | Svanberg et al. | 250/461.1 |
| 4,791,310 | 12/1988 | Honig et al. | 250/458.1 |
| 4,794,450 | 12/1988 | Saito et al. | 382/6 |
| 4,806,015 | 2/1989 | Cottingham | 422/73 |
| 5,071,247 | 12/1991 | Markosian et al. | 356/39 |
| 5,096,835 | 3/1992 | Yokomori et al. | 364/555 |
| 5,230,026 | 7/1993 | Ohta et al. | 382/6 |
| 5,233,668 | 8/1993 | Yokomori et al. | 382/6 |
| 5,234,665 | 8/1993 | Ohta et al. | 382/6 |
| 5,265,169 | 11/1993 | Ohta et al. | 364/413.01 |

OTHER PUBLICATIONS

McIntire et al., "Mechanical and Biochemical Aspects of Leukocyte Interactions With Model Vessel Walls," *White Cell Mechanics: Basic Science and Clinical Aspects*, 1984, 209–219.

McIntire et al., "Visualizing Clots on Artificial Surfaces," *Mechanical Engineering*, Jan. 1986, 32–35.

Rothlein et al., "A Human Intercellular Adhesion Molecule (ICAM–1) Distinct From LFA–1", *The Journal of Immunology*, 1986, 1270–1274.

Lawrence, et al., "Effect of Flow on Polymorphonuclear Leukocyte/Endothelial Cell Adhesion," *Blood*, Nov. 1987, 1284–1290.

Marlin, et al., "Purified Intercellular adhesion Molecul–1 (ICAM–1) Is a Ligand for Lymphocyte Function–Associated Antigen 1 (LFA–1)," *Cell*, Dec. 1987, 813–819.

Martz, "LFA–1 and Other Accessory Molecules Functioning in Adhesions of T and B Lymphocytes," *Human Immunology*, 1987, 3–37.

*Primary Examiner*—Joseph Mancuso
*Assistant Examiner*—David Fox
*Attorney, Agent, or Firm*—Arnold, White & Durkee

[57] ABSTRACT

A method and apparatus for the analysis of magnified video image data to develop quantitative functional and morphological indices for cell-to-cell adhesion. Such induces permit distinction between different adhesion modalities and identification of various adhesion pathways of cells, for example lymphocytes time resolved measurements can also be done to track individual cells or cell clusters.

12 Claims, 9 Drawing Sheets

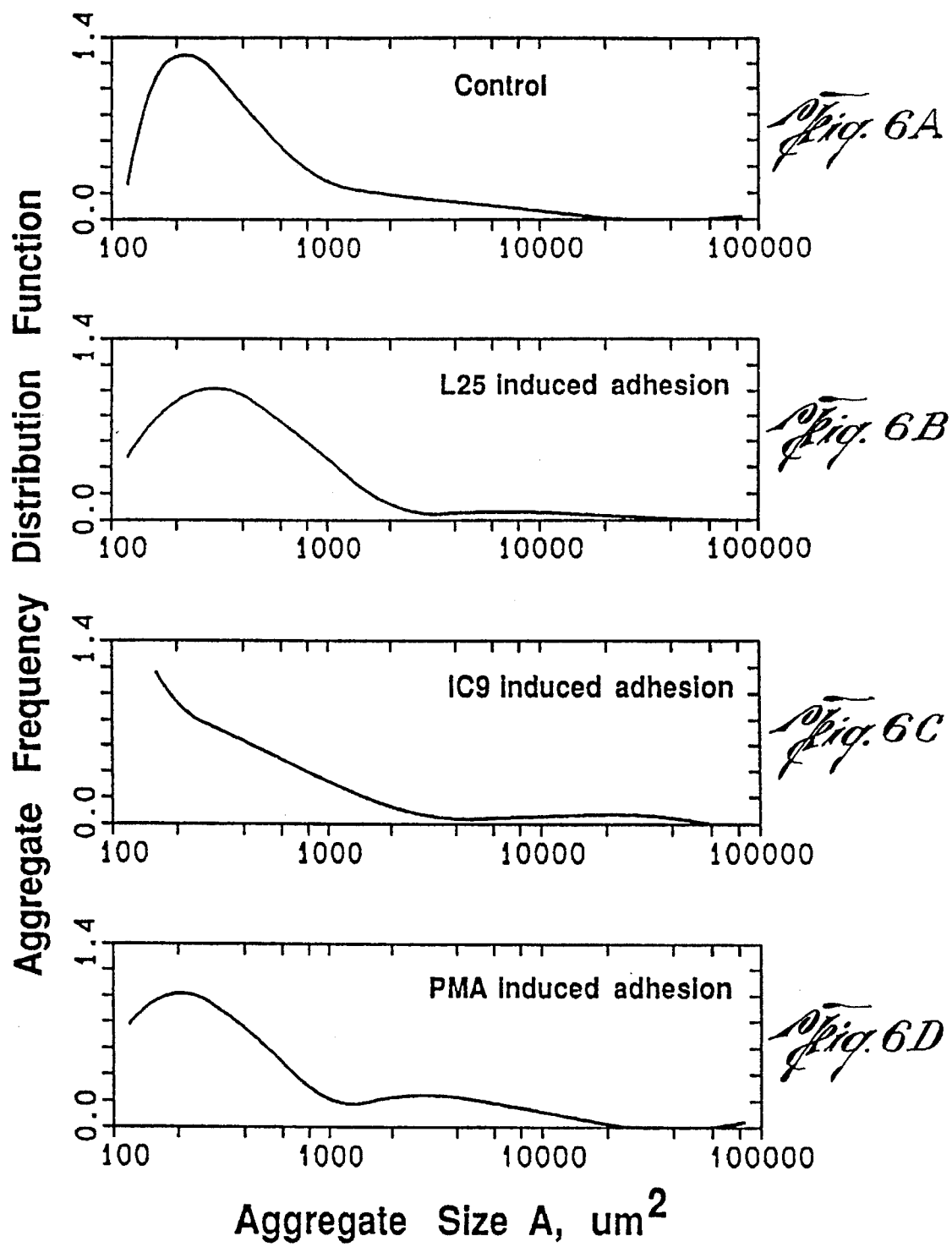

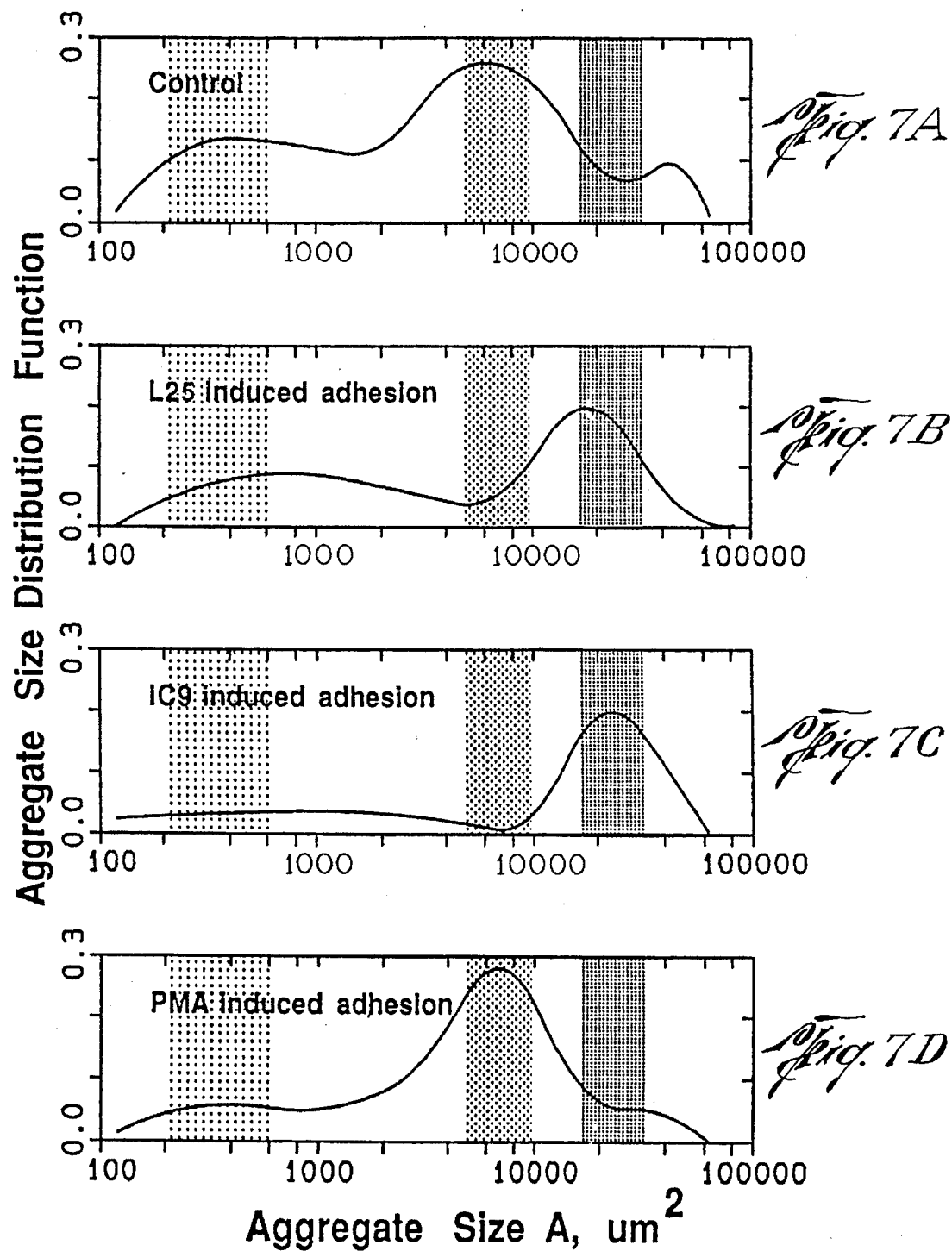

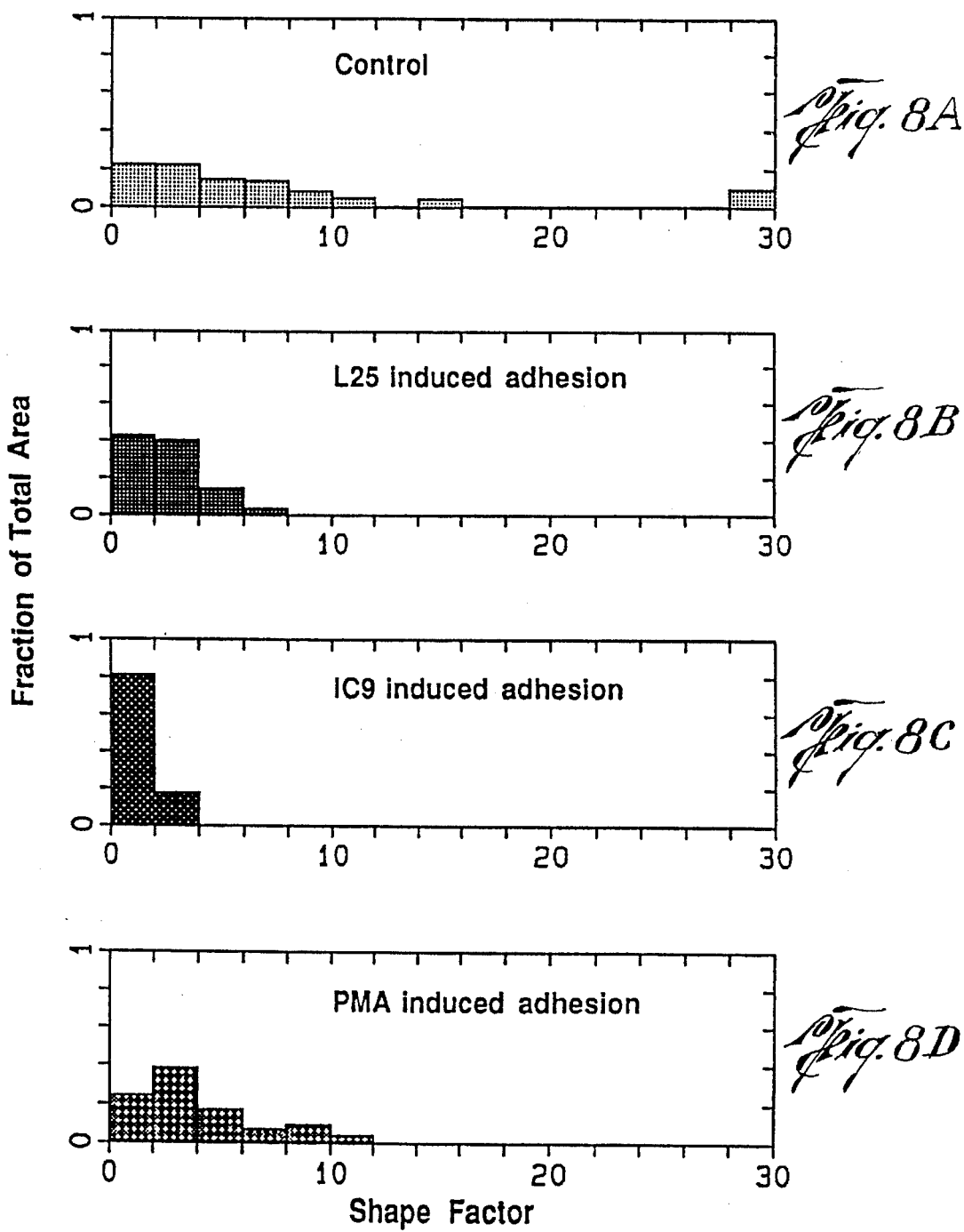

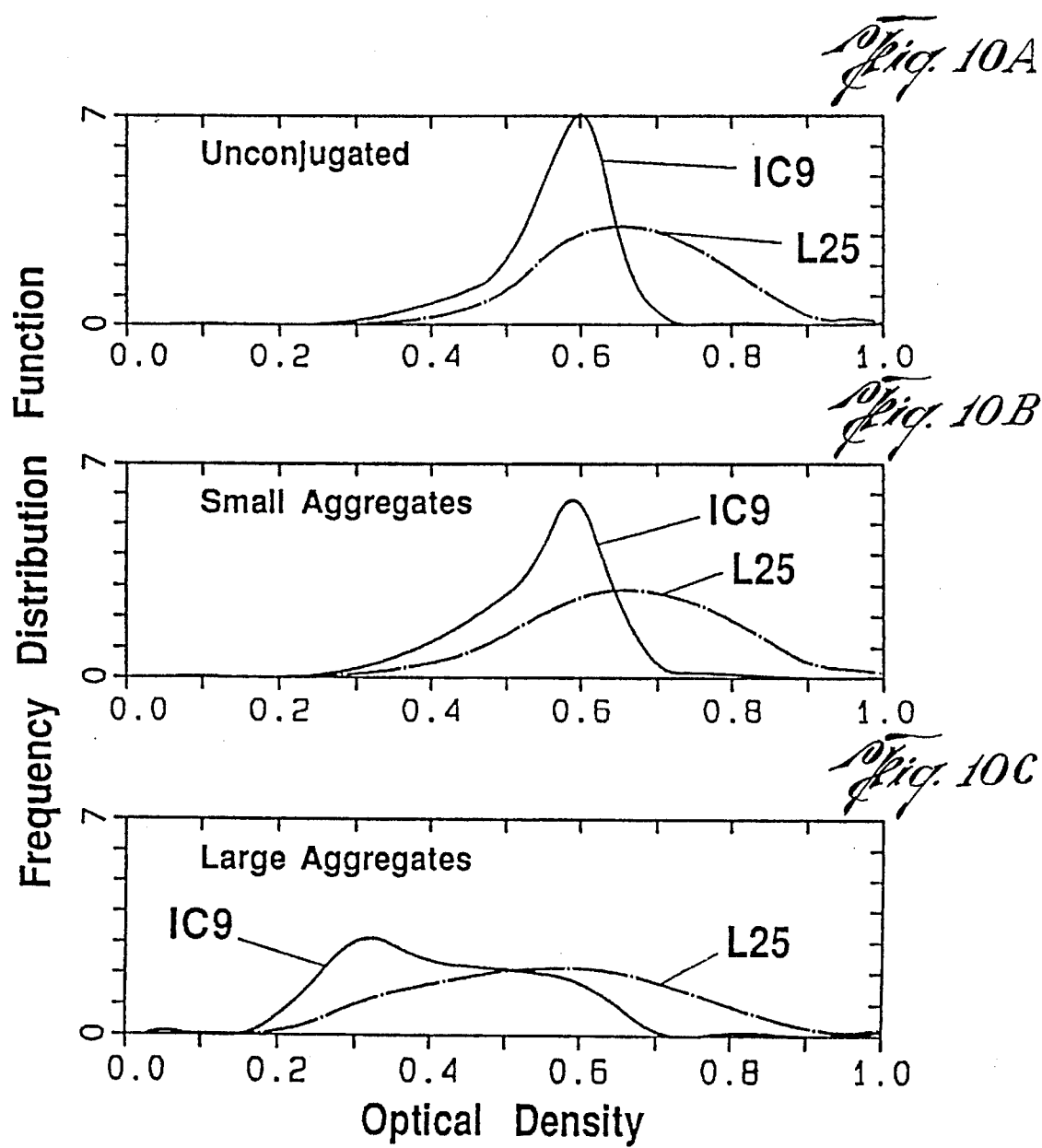

METHOD AND APPARATUS FOR TIME-RESOLVED MEASUREMENTS OF LYMPHOCYTE FUNCTION AND AGGREGATE STRUCTURE USING COMPUTER-AUTOMATED MICROSCOPY

BACKGROUND OF THE INVENTION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The invention relates to a method and apparatus for time-resolved measurements of lymphocyte function and cell aggregate structure using computer-automated microscopy.

Presently accepted methods for quantifying adhesion mechanics among cell aggregates are insensitive to the fine details of molecular pathways and structures which govern the cell aggregation process. Current methods of data presentation loose much information, and many physical characteristics of the aggregated cells which are important to the understanding of cell adhesion mechanics are never considered.

Known methods for quantifying cell aggregation often blur the distinction between aggregate shapes by use of rather simplistic, subjective scoring methods. For example, one known method for quantifying aggregate structure is through the use of a relative number scale presented below.

1+=<10% of cells in small aggregates (5–10 cells/clump)

2+=10–40% of cells aggregated (size varies)

3+=40–90% of cells aggregated (size varies)

4+=>90% of cells aggregated, usually in medium to large clumps

5+=approximately 100% of cells aggregated in large clusters

In order to eliminate the effects of personal bias, assays using this number scale are usually scored double-blind. While this has proved somewhat helpful in eliminating errors resulting from the subjectivity of the observer, the scoring method is still subject to human error and to variability between the perception of different observers. More importantly, this number scale does not reflect the potential differences in the physical dynamics or morphology that may exist between various adhesion events.

For example, using this number scoring method, adhesion induced in a human lymphoblastoid T-cell line, JURKAT, by anti-VLA-4 antibody was 5+, adhesion induced by the lectin PHA (phytohemagglutinin) was 5+, while adhesion induced by the phorbolester PMA (phorbol 12-myristate 13-acetate) was scored a 4+. These similar number scores occur despite the fact anti-VLA-4 induced aggregates are large round and compact, with very few free non-aggregated cells, aggregates induced by PHA are long-chained structures, and those induced by PMA are smaller, more loosely structured and contain far more non-aggregated cells. Stated otherwise, application of the known number scoring method to these three aggregate structures results in very similar numerical scores despite a markedly different appearance of the aggregates.

Another limitation of the simplistic numerical scoring method is the inability to establish rates of aggregate formation. Again, this results in a substantial loss of important information. For example, two antibodies that induce lymphocyte adhesion have recently been discovered; L25 (anti-VLA-4) and IC9 (ligand presently unknown). Both antibodies induce 5+ adhesion, but it has been observed that the rate of IC9-induced aggregation is considerably faster than that of L25-induced adhesion. A complete understanding of the different adhesion mechanisms induced by these two antibodies requires assessment of the relative rates of aggregation, an assessment which is not possible using presently available methodologies.

SUMMARY OF THE INVENTION

The present invention avoids the above-noted drawbacks of the prior art by quantifying morphological features of cell aggregates with several new structural measurements obtained by digital image analysis. The invention involves obtaining magnified images of cell aggregates, digitizing and filtering the images, segmentation of the processed images to identify the aggregates, and analysis of the segmented images to determine size, perimeter, shape and texture of each aggregate within the images.

The new structural measurements of the present invention include aggregate size distribution, aggregate size frequency distribution, aggregate shape factor distribution, the coverage of the image area by cell aggregates, and the integral optical density of the digitized image. These new structural measurements offer information regarding the size distribution, texture, shape and optical density of the cell aggregates, and also provide an indication of the percentage of the total image area that is covered by aggregates. These new parameters provide additional information which is useful in classifying subtle differences in the character of aggregation in various cell and induction systems, and may provide new insight regarding the physical and molecular bases of each.

The apparatus of the present invention includes a television camera for producing a video image of a magnified number of cell aggregates, a digitizer for digitizing the video image, and a computer for analyzing the digitized images, and for calculating the above structural parameters.

In addition, in order to assess the time rate of cell aggregation, a number of video images can be taken at spaced apart time intervals, and the structural parameters can be calculated for each image in the sequence. This will provide cell aggregation rate information, also valuable in morphological studies.

BRIEF DESCRIPTION OF THE DRAWINGS

FIGS. 6A–D are graphs of the aggregate frequency distribution parameter of the present invention calculated for the cell aggregations of FIGS. 5A–D.

FIGS. 7A–D are graphs of the aggregate size distribution parameter of the present invention calculated for the cell aggregate structures of FIGS. 5A–D.

FIGS. 8A–D are graphs of the shape factor parameter of the present invention calculated for the cell aggregate structures of FIGS. 5A–D.

FIGS. 10A–C are graphs of the integral optical density parameter of the present invention.

DETAILED DESCRIPTION

Figure 1:
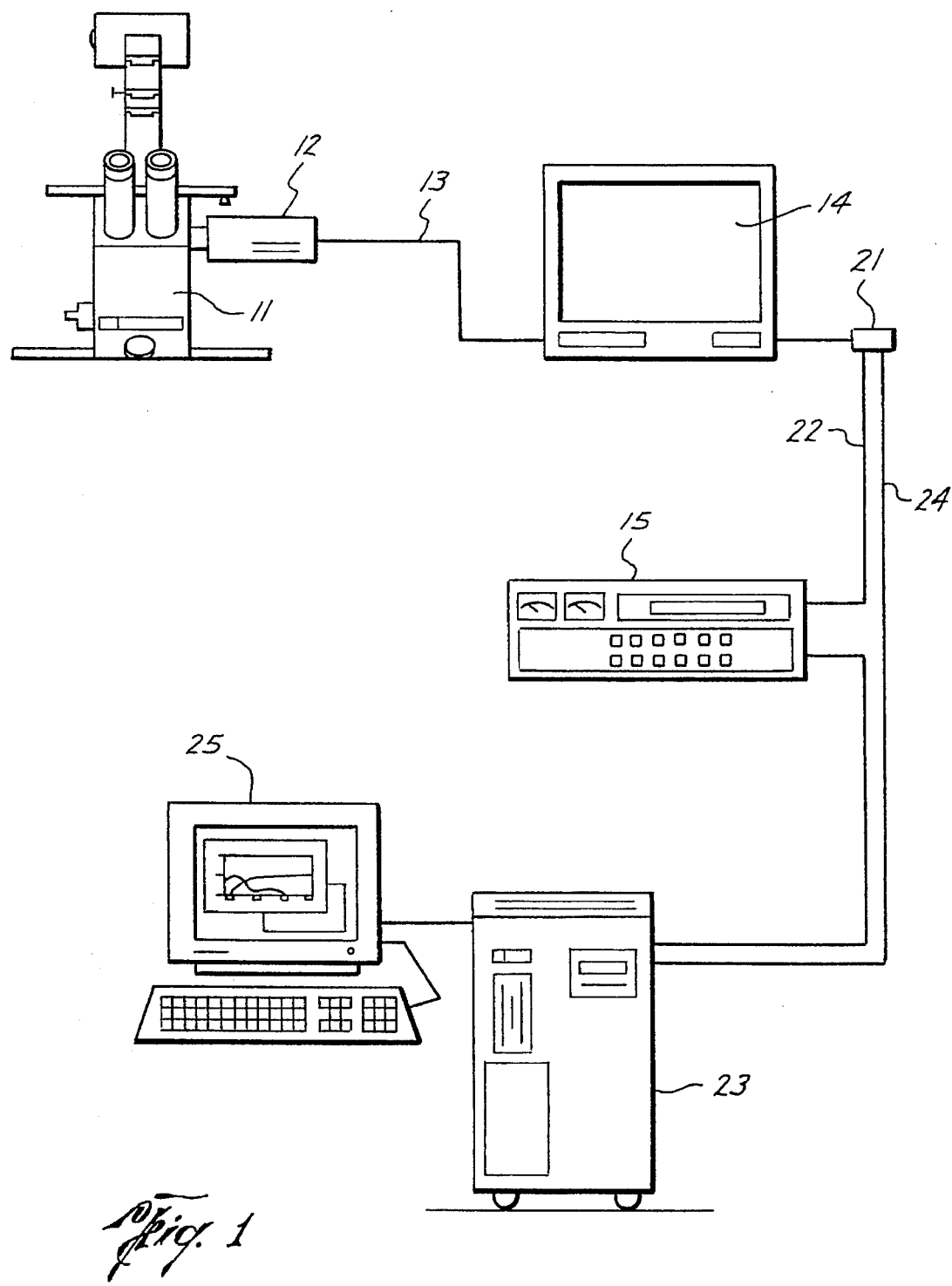
FIG. 1 is the apparatus of the present invention used to practice the method of the present invention.

Referring to FIG. 1, an apparatus according to the present invention which operates according to the method of the present invention is disclosed. Connected to inverted microscope 11 is video camera 12 which produces on line 13 NTSC video signals of the magnified image produced by microscope 11.

Cell aggregates under study are preferably contained within Terasaki plastic plates with inverted frusto-conical tapered wells having a 1.3 mm diameter bottom and a 3.9 mm diameter top. According to the preferred method of the present invention, a single drop of 1.5 microliters from a cell suspension is placed with a pipette on the bottom of each well in the Terasaki plate. It has been determined that volumes of cell suspension larger than 1.5 microliters lead to uneven distribution of the cells on the bottom of the well, with the majority of cells near the periphery of the well. This non-uniformity leads to erroneous results.

An appropriate reagent which induces or inhibits cell aggregation is placed in each of the wells, and the Terasaki plate is incubated at an appropriate temperature. The Terasaki plate is then placed on the stage of microscope 11.

Microscope 11 preferably has a 10× objective which provides a 1.00×0.75 millimeter field of view covering almost the entire cross section of an individual well in the Terasaki plate.

Figure 2:
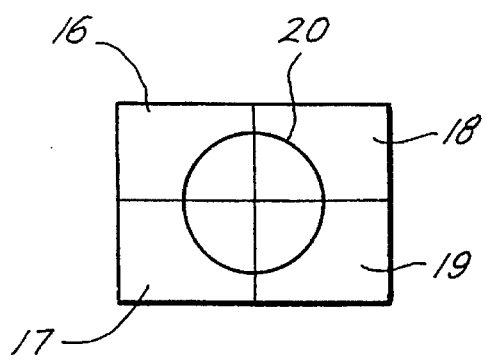
FIG. 2 illustrates the image acquisition of the present invention.

Referring also to FIG. 2, four images 16, 17, 18 and 19 of the well are taken in order to provide complete imaging of the cell aggregates on bottom 20 of each individual well of the Terasaki plate. The images are later combined during data processing to form a single image that contains all cells in a particular well.

Images are taken at various times and analyzed, or can be recorded by, for example, video cassette recorder 15. Video monitor 14 can be used to confirm the images produced by video camera 12. Video switch 21 is used to direct video images from camera 12 to recorder 15 through line 22, or for direct application to computer 23 through line 24.

Computer 23 can be, for example, a VAXstation II/GPX computer, available from Digital Equipment Corporation. Computer 23 is equipped with a video image digitizer board, for example a FG100 image digitizer available from Imaging Technologies, Inc., which digitizes the analog images provided by camera 12 into 640×480 8-bit pixels thereby providing 256 grey levels for each pixel. Preferably a total of 6 wells are imaged in order to obtain good population statistics.

Figure 4:
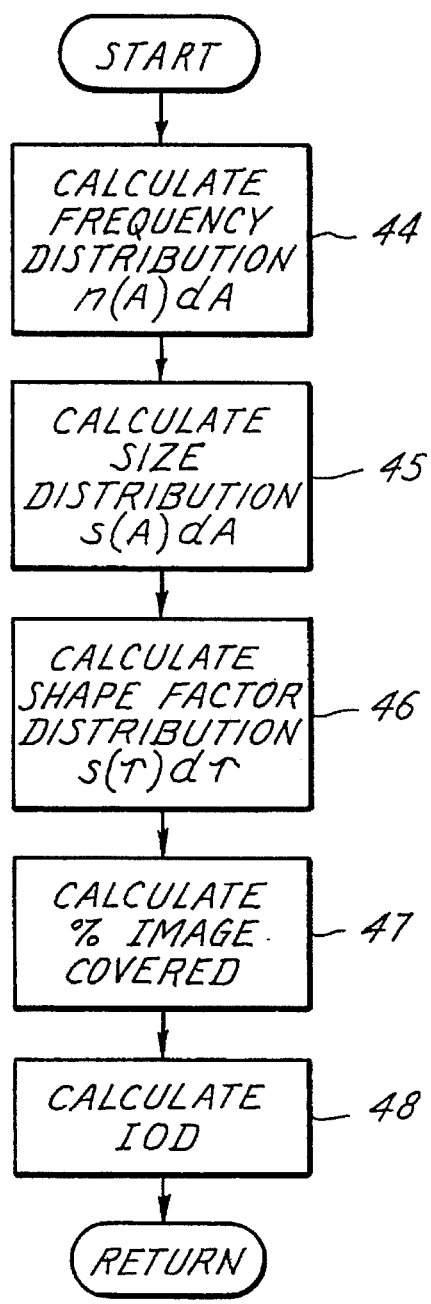
FIG. 4 is a flow chart of the calculation of the morphological indices of the present invention.
Figure 3:
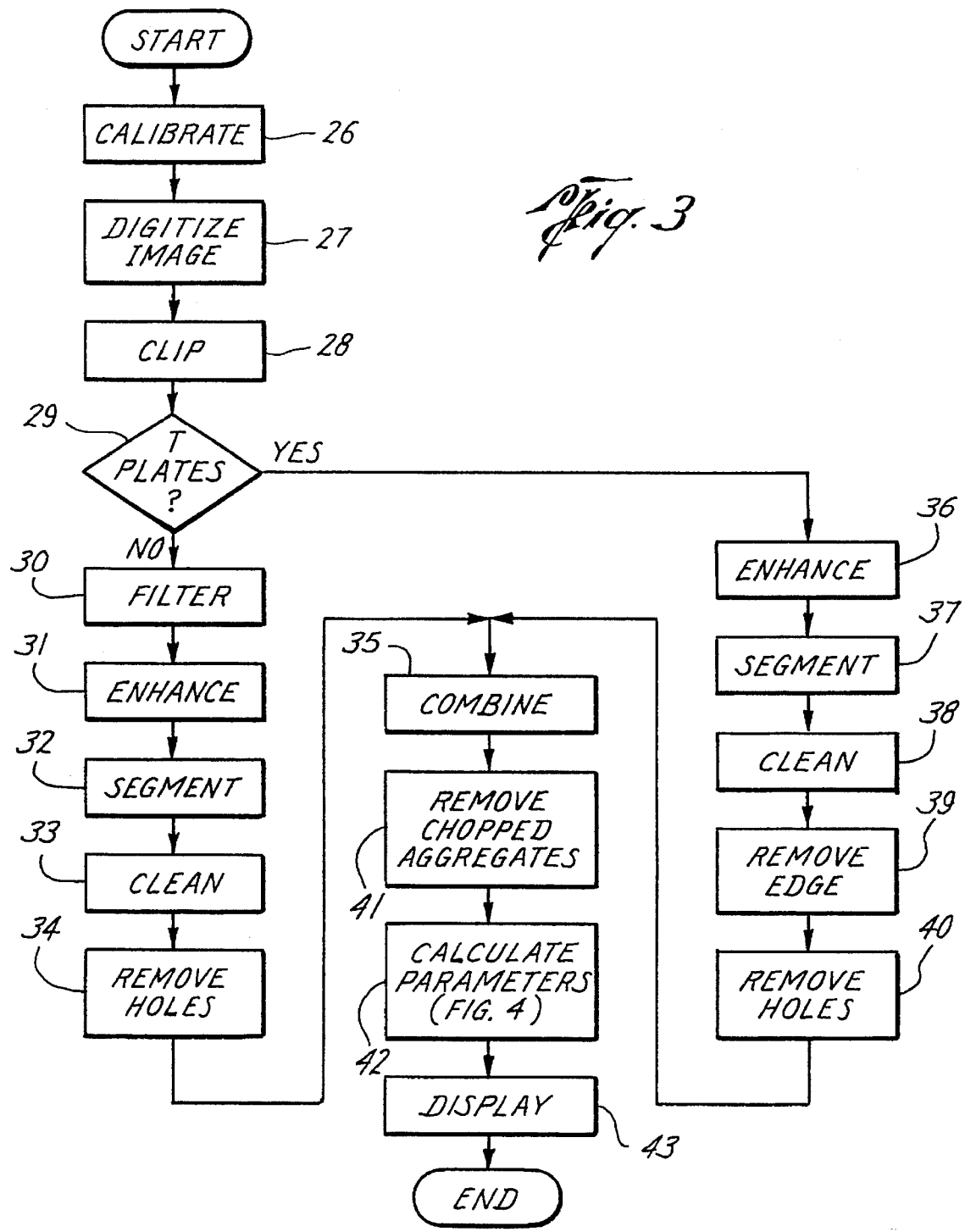
FIG. 3 is a flow chart of the operation of the apparatus of FIG. 1.

The combined four images (FIG. 2) are then analyzed in computer 23 according to the procedures described in the flow charts of FIGS. 3 and 4, to calculate the morphological indices of the present invention in order to assess aggregate structure and lymphocyte function. The morphological indices can be displayed in histogram form on video display terminal 25.

Referring to FIG. 3, the operation of computer 23 according to the present invention is disclosed in flow chart form.

Most of the procedures shown in FIG. 3 are preferably embodied in a commercially available image processing software package, Icoemtrics, available from Everest Technologies. Calculation of the specific aggregate structural parameters according to the present invention is shown in block 42 of FIG. 3, in slightly more detail in flow chart form in FIG. 4, and in the form of a source code computer program at the end of this specification.

Referring to FIG. 3, beginning in block 26, a calibration routine is performed in order to automatically accommodate variations in the magnification power of microscope 11. Control is then transferred to block 27 where the image digitizer within computer 23 is activated to digitize the video image. Then, in block 28, the digitized video image is clipped to remove black lines that occasionally appear around the boarders of the digitized image. Control then passes to decision block 29 where it is determined whether the video image is derived from the wells of a Terasaki plate. If not, control passes to block 30 where the digitized image is filtered with an averaging filter using a 3×3 kernel, and by a gradient filter with a 3×3 neighborhood. Control then passes to block 31 where image enhancement is performed by multiplying the image by itself using double precision arithmetic and then compressing again to 8-bits per pixel. Control then passes to block 32 where the grey levels of the image are segmented. In block 33, the image is eroded and dilated twice to smooth aggregates and to eliminate small one- or two-pixel objects that are due to pixelization errors and video noise. Control then passes to block 34 where the image is processed to remove holes appearing in the middle of cell aggregates. Control then passes to block 35 where images from several different cell cultures are combined to provide good population statistics.

On the other hand, if decision block 29 determines that Terasaki plates are used to produce the image, control passes to blocks 36, 37 and 38 which perform functions identical to blocks 31, 32 and 33, described above. Control then passes to block 39 where the portion of the image corresponding to the circular edge of the Terasaki plate is removed. Holes are then removed from within the image of the cell aggregates in block 46, using an identical procedure as that of block 34.

After images are combined in block 35 to improve cell population statistics, control passes to block 41 where objects within the image which are attributable to partially visible aggregates at the edges of the image are removed. Thus, the image contains only complete aggregates found in the field of view, thereby preventing erroneous morphological analysis by including artificially chopped aggregate images.

Finally, control passes to block 42 for calculation of the structural parameters of the present invention (described in more detail referring to FIG. 4), and the parameters are then formatted for display in block 43.

Referring to FIG. 4, the calculation of the specific structural parameters of the present invention is disclosed. The source code computer program appearing at the end of this specification presents the details of these procedures. In block 44, the frequency distribution function, n(A), for aggregate profiles is calculated, where A is the size, in $\mu m^2$, of the aggregate profiles or unconjugated cells identified and measured during digital image analysis. The frequency distribution function n(A) is defined as:

n(A)dA=fraction of aggregates with area between A and A+dA

Then, in block 45 the cell aggregate size distribution function, s(A) is calculated according to the following equation:

s(A)dA=fraction of total area $A_t$ that is attributable to aggregates with area between A and A+dA Where $A_t$ is the sum of the area of all aggregates in the image. Next, in block 46, the shape factor, τ, for each cell aggregate in the image is calculated according to the equation:

$$\tau = \frac{P^2}{4\pi A}$$

Where: P is the perimeter of the aggregate and A is its area. This descriptor takes its minimum value of one for a circle. Then, also in block 46, the shape factor distribution function s(τ) is calculated according to the equation:

s(τ)dτ=fraction of total area that is attributable to aggregates with a shape factor between τ and τ+dτ

Next, in block 47, the coverage, C, of the image area is calculated according to the equation:

$$C = A_t/A_{img}$$

Where: $A_t$ is the area in the image covered by aggregates or unconjugated cells, and $A_{img}$ is the total image area.

Finally, in block 48, the integral optical density descriptor, IOD, is calculated according to the equation:

$$IOD = \Sigma \frac{d\, m(d)}{m_t}$$

Where m(d) is the number of pixels having an optical density, or grey level, d, and where $m_t$ is the total number of pixels in the area of interest. Low values of optical density, which correspond to dark internal areas, indicate the formation of multi-layer aggregates.

Control is then returned to the routine of FIG. 3 for display of the results.

FIGS. 5–9 illustrate a specific application of the present invention. The computer-generated images of FIGS. 5A–D correspond, respectively, to the aggregates of JY cells using different induction protocols. Specifically, FIG. 5A is the control and illustrates spontaneous aggregation of JY cells. FIG. 5B illustrates aggregation induced by L25 (anti-VLA-4). FIG. 5C is aggregation induced by IC9 (ligand presently unknown), and FIG. 5D is PMA (phorbol 12-myristate 13-acetate) induced aggregation. All four images were obtained four hours after the start of the experiment. By visual observation, it can be seen that the aggregates of FIGS. 5A–D exhibit a wide sized distribution, and the that the different aggregate induction protocols produce aggregates with widely different morphologies.

Figure 5A:
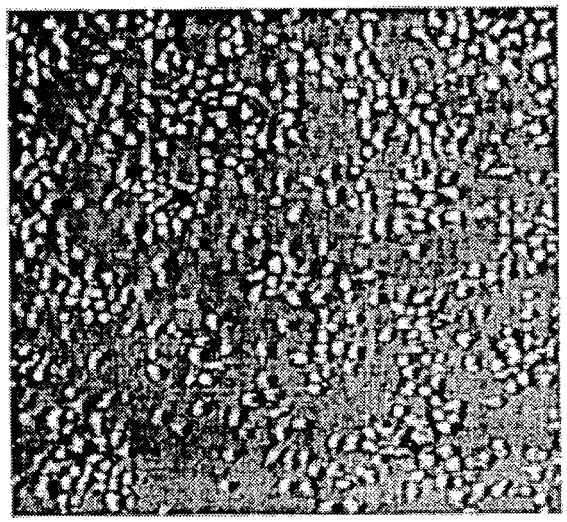
FIGS. 5A–D are computer-generated images of different aggregated cell structures used to illustrate the present invention.

In the control, FIG. 5A, aggregates are chain or chain-bead structures and almost all appear to consist of a single layer. A large fraction of the cells do not form aggregates.

Figure 5B:
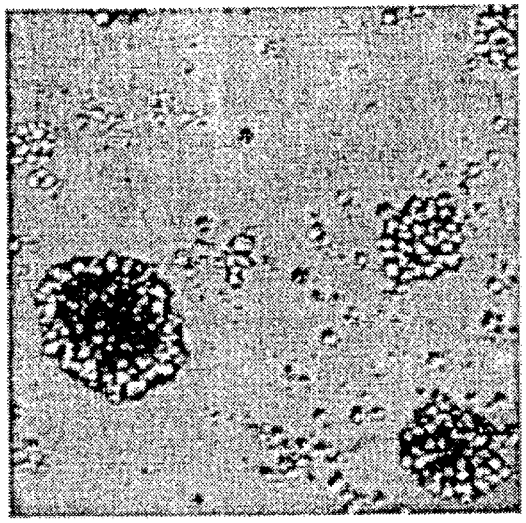

In the L25-induced adhesion of FIG. 5B, aggregates are large beads with very few short-chained structures. Many aggregates are dark in the middle with a characteristic bright single-cell ring around their periphery. Such aggregations are most likely piles of cells including several layers of cells, but this 3-dimensional structure cannot be confirmed by using standard light transmission microscopy.

Figure 5C:
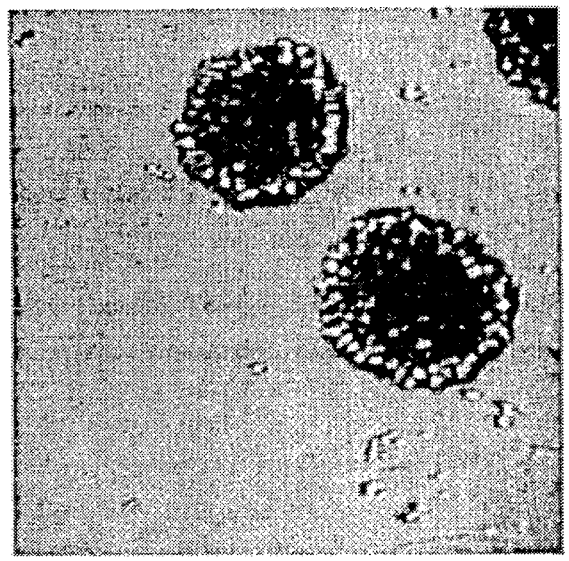

The IC9-induced adhesion of FIG. 5C illustrates aggregates that are almost exclusively large multi-layered clusters, with very few unconjugated cells or single-layer clusters.

Figure 5D:
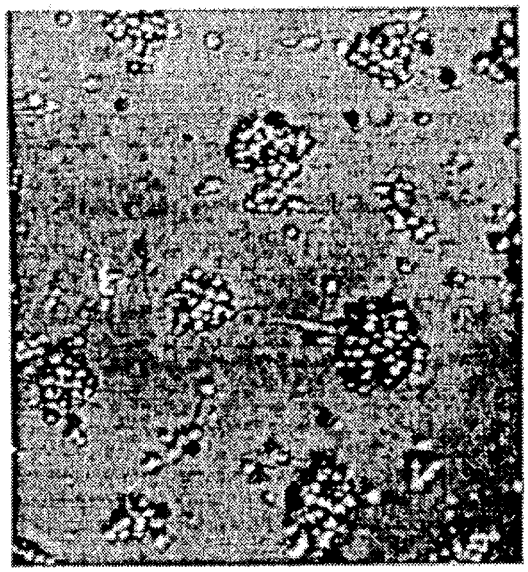

The PMA-induce adhesion aggregates shown in FIG. 5D include aggregates which are circular and rather small, consisting of only a single, or possibly two, layers of cells.

By application of the present invention, the graphs shown in FIGS. 6–10 result.

FIGS. 6A–D present the frequency distribution functions, n(A)dA, respectively computed for the four adhesion protocols shown in FIGS. 5A–D. All four distributions exhibit a maximum in the range of 200–400 µm². This corresponds to unconjugated JY cells. Also, all plots show a relatively small fraction of conjugates with sizes greater than 2000 µm² with the possible exception of PMA-induced aggregation, which exhibits a maximum of around 3000 µm². The plots of FIG. 6 are notable for their lack of a distinguishing characteristics. The similarities between the plots obtained for spontaneous adhesion and for L25-induced adhesion are particularly striking given the totally different structures of the aggregates in those cases (FIGS. 5A and B).

The size distribution functions, s(A)dA, shown respectively in FIGS. 7A–D, on the other hand, clearly indicate significant morphological differences among the aggregates obtained with the four different protocols. Referring to FIG. 7A, with spontaneous adhesion, several distinct peaks are identified. The first peak occurs in the 200–400 µm² range and corresponds to unconjugated cells. After a plateau, indicating the presence of the small clusters with 5–10 cells each, a second peak appears in the 4000–10,000 µm² range. The third peak is actually due to several smaller clumps or chains that have joined together to form chain-bead and highly tortuous structures.

In the L25-induced adhesion of FIG. 7B, one major peak in the 10,000–40,000 µm² range corresponds to large aggregates. A substantial amount of unconjugated and small clusters is indicated by a broad smaller peak extending from 200–3,000 µm².

FIG. 7C, IC9-induced adhesion, exhibits a peak corresponding to large aggregates that is higher, narrower and slightly shifted toward larger areas. This indicates very few unconjugated cells and clumps.

Finally, PMA-induced adhesion, shown in FIG. 7D, is similar to the control of FIG. 7A and exhibits three peaks. The first is mostly attributed to unconjugated cells. The major peak appears in the 8,000–10,000 µm² range and corresponds to medium-sized clumps. A much smaller peak at 30,000 µm² indicates the presence of a few large clusters.

Turning to the graphs of the shape factor distribution function, s(τ)dτ, for the four different protocols shown FIG. 8A–D, IC9-induced adhesion (FIG. 5C) leads to aggregates with almost circular profiles (over 90% of the aggregates having shape factors between 1 and 2), while L25-induced adhesion (FIG. 5B) has a wider distribution, and the aggregates produced by the control (FIG. 5A) and by PMA-induced adhesion (FIG. 5D) are rather loose structures having shape factors exceeding the value of 10.'

Figure 9:
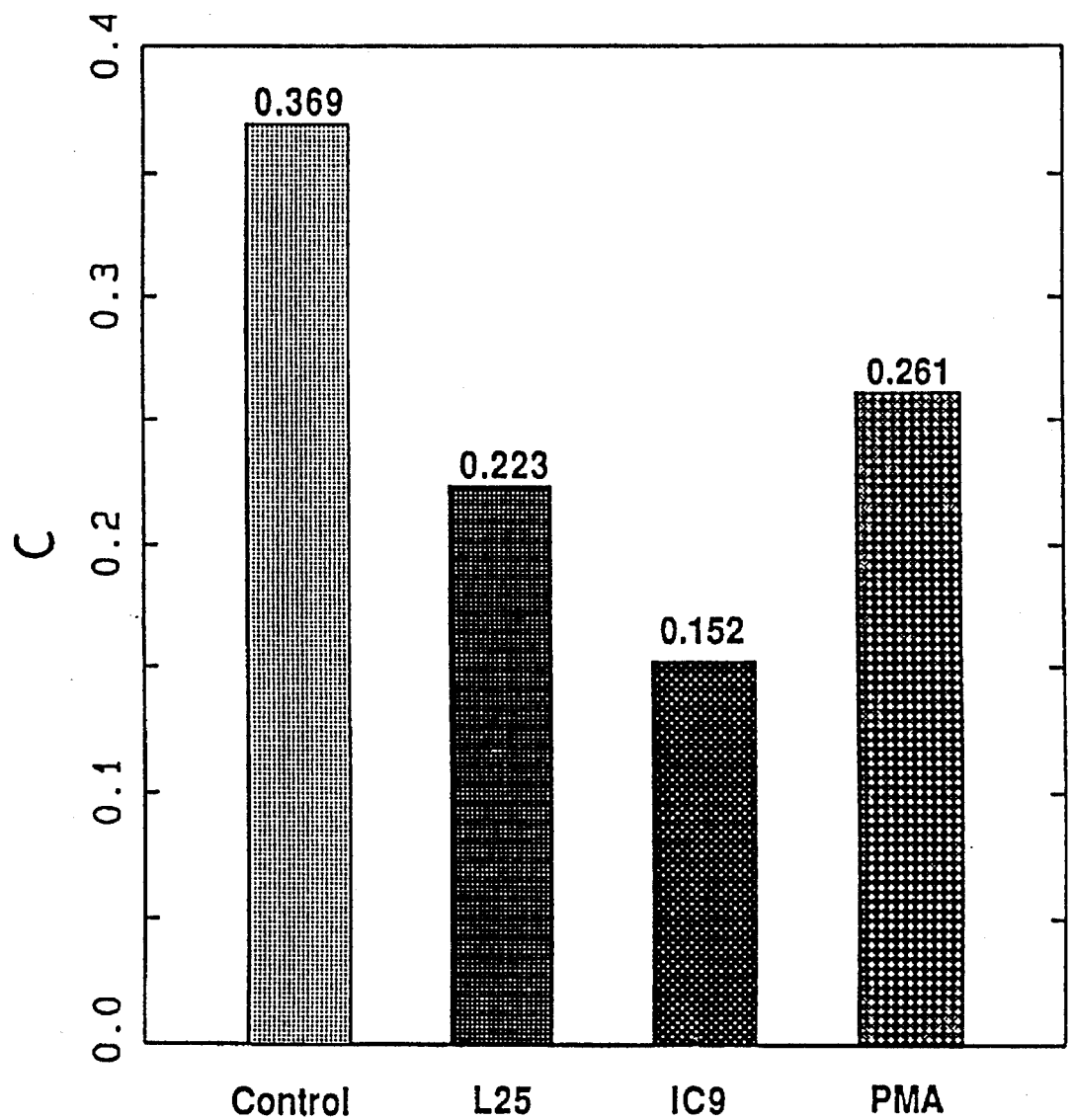
FIG. 9 is a graph of the fraction of image area covered by aggregates for the cell aggregates structures of FIGS. 5A–D.

FIG. 9 shows the coverage, C, computed for the four cases of adhesion. The smallest coverage is observed for IC9-induced adhesion, indicating a tight-packing of cells in the aggregates, possibly in a 3-dimensional multi-layered arrangement.

FIGS. 10A–C is the frequency distribution function of optical density for unconjugated, small aggregates, and large aggregates, respectively, showing aggregates of both IC9-induced and L25-induced adhesion (FIGS. 5C and B, respectively).

The time rate of cell aggregation also provides valuable information regarding the physical and molecular events underlying the adhesion process. The morphological indices of the present invention can be calculated for each image of a time-sequence of images of a cell suspension undergoing aggregation, thereby providing objective cell aggregation information as a function of time.

The present invention which quantifies lymphocyte adhesion is insensitive to possible differences in the physical and molecular events which govern the adhesion process. Consequently, the assay can be used to classify subtle differences in the character of lymphocyte aggregation in various cell and induction systems. The results provide new insight regarding the physical and molecular bases of each, and allow investigation of several issues.

For example, evaluation of digital images of aggregation induced with and without the presence of monoclonal antibodies to various surface molecules provides an increased chance to observe any aggregation inhibition. Any change in the structural parameters measured by the present invention due to the addition of a particular monoclonal antibody would indicate that the corresponding antigen was involved.

In addition, it is presently hypothesized that magnetism, and not calcium, is required for LFA-1 dependent adhesion to occur. The increased sensitivity of the image analysis of the present invention will provide a more rigorous test for this hypothesis.

Also, the techniques of the present invention can be used to investigate synergism between different modes of adhesion induction. For example, if PMA-induced adhesion is a completely committed process, the addition of L25 or IC9 will not alter the character of the adhesion. In other words, once cells are committed to a PMA-induced adhesion process, other adhesion inducers would have no affect, and the structural parameters of the present invention would indicate that the adhesion event occurred like normal PMA-induced adhesion. On the other hand, if PMA- and IC9-induced adhesion are complementary, lymphocytes exposed to both induction methods should demonstrate more complete aggregation than either induction protocol alone. However, if IC9- and PMA-induction mediated adhesion through identical mechanisms, then lymphocytes exposed to both adhesion inducers will exhibit adhesion characteristics for the most efficient process, in this case IC9.

These examples of specific applications of the present invention to assess adhesion mechanics will be understood by those of skill in the art to be merely exemplary, and not limiting of the present invention. In addition, one of skill in this art will appreciate that changes, additions and modifications can be made to the apparatus of the present invention, and that different apparatus can be used to practice the method of the present invention, without departing from the spirit and scope of this invention.

The following is a source code listing of a computer program for computer 23 of FIG. 1, and details the procedures shown in flow-chart form in FIG. 4.

CLIO$DUB4:[CONTROL.TOOLKIT]BAR.FOR

```fortran
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%%%
C
C       PROGRAM BAR
C
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%;%%%%%%%%%%%%%%%%%%%%%%%%%%%%%%%%%%%%%%*
C
C       COPYRIGHT (c) 1989 by Kyriacos Zygourakis
C       ALL RIGHTS RESERVED
C
C       Written by Kyriacos Zygourakis
C
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%;%%%%%%%%%%%%%%%%%%%%%%%%%%%%%%%%%%%%%%
C
C       This program analyzes raw data (object measurements) produced
C       by the ICOMETRICS system
C       ICOMETRICS Menu: ANALYZE (Save statistics)
C
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%%%

DIMENSION TEMP(16), X(20000), AREA(20000), RAD(20000)
        DIMENSION BIN_LIM(101), BIN_SUM(100), BIN_POP(100)
        DIMENSION BIN_SUM_CUM(100), BIN_POP_CUM(100)
        INTEGER*4 BIN_COUNT(100), CHECK_COUNT
        CHARACTER*40 DATAFILE, BARFILE
        CHARACTER*6 UNITS
        CHARACTER*16 XPROP(16)
        INTEGER*4 LENXP(16), LENYP(2)
        LOGICAL XLOG, YESNO, CONMIN, CONMAX
C
        CALL LIB$GET_INPUT( DATAFILE, 'Statistics file ? ', LENDATA)
        INBRA=INDEX(DATAFILE,']')

INDOT=INDEX(DATAFILE(INBRA:LENDATA),'.')
        IF (INDOT.GT.0) LENDATA=INDOT-1
        DATAFILE=DATAFILE(1:LENDATA)//'.STAT'
C
        PI=ACOS(-1.0)
C
        OPEN(UNIT=15,FILE=DATAFILE,STATUS='OLD',READONLY)
        READ(15,91) UNITS
91      FORMAT(A)
        IF(UNITS(1:2).EQ.'5m') UNITS(1:2)='um'
        READ(15,*) NUMPROPS
        READ(15,92) (XPROP(I),I=1,NUMPROPS)
92      FORMAT(<NUMPROPS>A16)
        DO I=1,NUMPROPS
                LENXP(I)=INDEX(XPROP(I),' ')-1
        ENDDO
        READ(15,*) NUMOBJECTS
C
        IDA=0
        DO I=1,NUMPROPS
```

```
              IF(XPROP(I)(1·4).EQ.'Area') THEN
                    IDA=I
              ENDIF
        ENDDO
        WRITE(6,*)
        IF(IDA.EQ.0) STOP 'ERROR - Area is not reported !'
        IF(IDA.GT.0) WRITE(6,*) 'ID for Area : ',IDA
C
        WRITE(6,900)
900     FORMAT(/' Statistics for the following properties are reported:')
        DO I=1,NUMPROPS
              WRITE(6,902) I,XPROP(I)
902           FORMAT(5X,I3,' : ',A)
        ENDDO
        WRITE(6,903)
903     FORMAT( 7X,'0 : Area equivalent radius')
        WRITE(6,904)
904     FORMAT(/' ID for X-axis property ? ',$)
        READ(5,*) IDX
        IF(IDX.GE.1.AND.IDX.LE.NUMPROPS) THEN
              WRITE(6,910) XPROP(IDX)(1:LENXP(IDX))
910           FORMAT(/'....Reading data for ',A,' histogram')
        ENDIF
        IF(IDX.EQ.0) THEN
              WRITE(6,912)
912           FORMAT(/'....Reading data for equivalent radius histogram')
        ENDIF
        IF(IDX.GT.NUMPROPS) THEN
              WRITE(6,914)
914           FORMAT(/'ERROR - Invalid property ID')
              CALL EXIT
        ENDIF C
        XMIN=1.0E+35
        XMAX=1.0E-35
        AREA_MIN=1.0E+35
        AREA_MAX=1.0E-35
        KOUNT=0
        DO I=1,20000

READ(15,*,END=100) (TEMP(J),J=1,NUMPROPS)
              AREA(I)=TEMP(IDA)
              RAD(I)=SQRT(AREA(I)/PI)
              IF(IDX.GE.1) THEN
                    X(I)=TEMP(IDX)
                    IF(XPROP(IDX)(1:LENXP(IDX)).EQ.'Tortuosity') X(I)=X(I)*X
(I)
              ELSE
                    X(I)=RAD(I)
              ENDIF
              IF(X(I).LT.XMIN) XMIN=X(I)
              IF(X(I).GT.XMAX) XMAX=X(I)
              IF(AREA(I).LT.AREA_MIN) AREA_MIN=AREA(I)
              IF(AREA(I).GT.AREA_MAX) AREA_MAX=AREA(I)
              KOUNT=KOUNT+1
        ENDDO
        WRITE(6,*) 'WARNING - File has more than 20,000 objects'
C
100     CONTINUE
        IF(KOUNT.NE.NUMOBJECTS) WRITE(6,*) 'WARNING - KOUNT .NE. NUMOBJECTS'
```

```
            AREA_CON_MIN=0.0
            CONMIN=.FALSE.
            WRITE(6,915)
915         FORMAT(/' Constraint on minimum object area ? [N] ',$)
            IF(YESNO(-1)) CONMIN=.TRUE.
            IF(CONMIN) THEN
                    WRITE(6,916)
916                 FORMAT( ' Minimum object area allowed : ',$)
                    READ(5,*) AREA_CON_MIN
            ENDIF
C
            AREA_CON_MAX=1.0E+35
            CONMAX=.FALSE.
            WRITE(6,917)
917         FORMAT(/' Constraint on maximum object area ? [N] ',$)
            IF(YESNO(-1)) CONMAX=.TRUE.
            IF(CONMAX) THEN
                    WRITE(6,918)
918                 FORMAT( ' Maximum object area allowed : ',$)
                    READ(5,*) AREA_CON_MAX
            ENDIF
C
            IF(IDX.GE.1) THEN
                    WRITE(6,920) XPROP(IDX)(1:LENXP(IDX)),XMIN,
       1                         XPROP(IDX)(1:LENXP(IDX)),XMAX
920                 FORMAT(/' Minimum ',A,' = ',G12.5,/,
       1                    ' Maximum ',A,' = ',G12.5,/)
                    XLOG = .TRUE.
                    WRITE(6,921)
921                 FORMAT(/' Logarithmic X scale ? [Y] ',$)
                    IF(.NOT.YESNO(1)) XLOG = .FALSE.
                    WRITE(6,922) XPROP(IDX)(1:LENXP(IDX))
922                 FORMAT(/' Input minimum ',a,' value : ',$)
                    READ(5,*) UMIN
                    WRITE(6,924) XPROP(IDX)(1:LENXP(IDX))
924                 FORMAT( ' Input maximum ',a,' value : ',$)
                    READ(5,*) UMAX
            ENDIF
            IF(IDX.EQ.0) THEN
                    WRITE(6,9201) XMIN,XMAX 9201                FORMAT(/' Minimum radius = ',G12.5,/,
       1                    ' Maximum radius = ',G12.5,/)
                    XLOG = .TRUE.
                    WRITE(6,9211)
9211                FORMAT(/' Logarithmic X scale ? [Y] ',$)
                    IF(.NOT.YESNO(1)) XLOG = .FALSE.
                    WRITE(6,9221)
9221                FORMAT(/' Input minimum radius value : ',$)
                    READ(5,*) UMIN
                    WRITE(6,9241)
9241                FORMAT( ' Input maximum radius value : ',$)
                    READ(5,*) UMAX
            ENDIF
C
            WRITE(6,926)
926         FORMAT( ' Input number of bins : ',$)
            READ(5,*) NBIN
C
            IF(.NOT.XLOG) THEN
                    BINSIZE=(UMAX-UMIN)/FLOAT(NBIN)
```

```
                BIN_LIM(1)=UMIN
                DO I=2,NBIN+1
                        BIN_LIM(I)= BIN_LIM(I-1)+BINSIZE
                ENDDO
        ELSE
                DECADE=ALOG10(UMAX/UMIN)
                DECBIN=FLOAT(NBIN)/DECADE
                BIN_LIM(1)=UMIN
                DO I=2,NBIN+1
                        BIN_LIM(I)=UMIN * (10**(FLOAT(I-1)/DECBIN))
                ENDDO
        ENDIF
C
        DO I=1,NBIN
                BIN_SUM(I)=0.0
                BIN_COUNT(I)=0
        ENDDO
C
        AREA_SUM=0.0
        CON_AREA_SUM=0.0
        NUM_CON_OBJECTS=0
        DO I=1,NUMOBJECTS
C
                AREA_SUM=AREA_SUM+AREA(I)
                IF(AREA(I).GE.AREA_CON_MIN.AND.AREA(I).LE.AREA_CON_MAX) THEN
                        CON_AREA_SUM=CON_AREA_SUM+AREA(I)
                ENDIF
C
C       Find the interval where each object belongs to
C
                DO K=1,NBIN
                        IF(AREA(I).GE.AREA_CON_MIN.AND.AREA(I).LE.AREA_CON_MAX
     2                  .AND.X(I).GE.BIN_LIM(K).AND.X(I).LT.BIN_LIM(K+1)) THEN
                                BIN_SUM(K)=BIN_SUM(K)+AREA(I)
                                BIN_COUNT(K)=BIN_COUNT(K)+1
                                NUM_CON_OBJECTS=NUM_CON_OBJECTS+1
                        ENDIF
                ENDDO
        ENDDO
C CHECK_SUM=0.0
        CHECK_COUNT=0
        DO K=1,NBIN
                BIN_SUM(K)=BIN_SUM(K)/CON_AREA_SUM
                CHECK_SUM=CHECK_SUM+(BIN_SUM(K)*(CON_AREA_SUM/AREA_SUM))
                CHECK_COUNT=CHECK_COUNT+BIN_COUNT(K)
                BIN_POP(K)=FLOAT(BIN_COUNT(K))/FLOAT(NUM_CON_OBJECTS)
        ENDDO
C
        IF((1.0-CHECK_SUM).GT.1.0E-6) WRITE(6,940) 100*(1.0-CHECK_SUM)
940     FORMAT(/' INFO ! ',f8.4,'% of total area not included in '
     1   'specified range ')
        IF(CHECK_COUNT.NE.NUMOBJECTS) WRITE(6,942) NUMOBJECTS-CHECK_COUNT
942     FORMAT(/' INFO ! ',I6,' objects not included in specified range')
C
        DO K=1,NBIN
                BIN_SUM_CUM(K)=0.0
                BIN_POP_CUM(K)=0.0
                DO J=1,K
                        BIN_SUM_CUM(K)=BIN_SUM_CUM(K)+BIN_SUM(J)
```

```
                           BIN_POP_CUM(K)=BIN_POP_CUM(K)+BIN_POP(J)
                   ENDDO
           ENDDO
C
           TOT_AWPA=0.0
           IF(IDX.EQ.1) THEN
                   DO I=1,NBIN
                           BAVA=0.5*(BIN_LIM(I)+BIN_LIM(I+1))
                           TOT_AWPA=TOT_AWPA+BIN_POP(I)*BAVA
                   ENDDO
           ENDIF
C
           AVGAREA=AREA_SUM/FLOAT(NUMOBJECTS)
           AVGDIAM=SQRT(4.0*AVGAREA/PI)
           PWADIAM=SQRT(4.0*TOT_AWPA/PI)
C
           DIAMAX=2.0*SQRT(AREA_MAX/PI)
           DIAMIN=2.0*SQRT(AREA_MIN/PI)
C
           IF(IDX.GE.1) BARFILE=DATAFILE(1:LENDATA)//'_'//XPROP(IDX)(1:4)//'.HIST'
           IF(IDX.EQ.0) BARFILE=DATAFILE(1:LENDATA)//'_ERAD.HIST'
           WRITE(6,*)
           WRITE(6,*) '...Histogram data reported in ',BARFILE
           OPEN(UNIT=16,FILE=BARFILE,STATUS='NEW')
           IF(IDX.GE.1) WRITE(16,950) DATAFILE,NUMOBJECTS,CON_AREA_SUM,
          1        UNITS,DIAMAX,UNITS,DIAMIN,AVGDIAM,PWADIAM,XPROP(IDX)
 950       FORMAT(//' Statistics file          : ',A,/,
          1        ' Total number of objects : ',I6,/,
          1        ' Total area of objects    : ',g12.5,1x,'sq. ',a,//,
          2        ' Maximum equivalent diameter : ',g12.5,1x,a,/,
          3        ' Minimum equivalent diameter : ',g12.5,/,
          4        ' Average diameter (1)        : ',g12.5,/,
          5        ' Average diameter (2)        : ',g12.5,///,
          6        ' REPORTED PROPERTY : ',A,///,
          7        10X,'INTERVAL',10X,2X,'MID-POINT',2X,
          8        11X,'AREA FRACTION',6X,8X,'POPULATION FRACTION',/)
           IF(IDX.EQ.0) WRITE(16,951) DATAFILE,NUMOBJECTS,CON_AREA_SUM,
          1        UNITS,DIAMAX,UNITS,DIAMIN,AVGDIAM,PWADIAM
 951       FORMAT(//' Statistics file          : ',A,/,
          1        ' Total number of objects : ',I6,/,
          1        ' Total area of objects    : ',g12.5,1x,'sq. ',a,//,
          2        ' Maximum equivalent diameter : ',g12.5,1x,a,/,
          3        ' Minimum equivalent diameter : ',g12.5,/,
          4        ' Average diameter (1)        : ',g12.5,/,
          5        ' Average diameter (2)        : ',g12.5,///,
          6        ' REPORTED PROPERTY : Area equivalent radius',///,
          7        10X,'INTERVAL',10X,2X,'MID-POINT',2X,
          8        11X,'AREA FRACTION',6X,8X,'POPULATION FRACTION',/)
C
           IF(.NOT.XLOG) THEN
                   DO I=1,NBIN
                           WRITE(16,952) BIN_LIM(I),BIN_LIM(I+1),
          1                        0.5*(BIN_LIM(I)+BIN_LIM(I+1)),
          2                        BIN_SUM(I),BIN_SUM_CUM(I),
          3                        BIN_POP(I),BIN_POP_CUM(I)
                   ENDDO
           ELSE
                   DO I=1,NBIN
                           WRITE(16,952) BIN_LIM(I),BIN_LIM(I+1),
          1                        SQRT(BIN_LIM(I)*BIN_LIM(I+1)),
```

```
     2                         BIN_SUM(I),BIN_SUM_CUM(I),
     3                         BIN_POP(I),BIN_POP_CUM(I)
          ENDDO
        ENDIF
C
952     FORMAT( 1X,G12.5,' - ',G12.5,1X,G12.5,5X,
     2          1X,G12.5,1X,G12.5,
     3          1X,G12.5,1X,G12.5)
        WRITE(16,952) BIN_LIM(NBIN+1),BIN_LIM(NBIN+1),BIN_LIM(NBIN+1),
     1                ZERO,ZERO,ZERO,ZERO
        CLOSE(16)
C
        WRITE(6,953) 100*CHECK_SUM,CHECK_COUNT
953     FORMAT(/' ---------------------------------------',/,
     1         ' REPORT TOTALS : Area Fraction  : ', F6.2,' %',/,
     2         '                 Object Count   : ', I6,/,
     3         ' ---------------------------------------')
C
        STOP
        END
```

CLIO$DUB4:[CONTROL.UTIL]SMOOTH_LOG.FOR

```
C%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%
C
        SUBROUTINE USER_FUNC(X,Y,N)
C
C%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%
C
C       COPYRIGHT (c) 1989 by Kyriacos Zygourakis
C       ALL RIGHTS RESERVED
C
C       Written by Kyriacos Zygourakis
C
C%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%
C
C       This subroutine is a USER_FUNCTION for the CCPLOT plotting
C       package (see manual of CCPLOT v. 3.0 for details on usage)
C
C       It takes a set of (X,Y) points, transforms the X values so that
C       we will come up with a semilog plot (X axis - logarithmic, Y axis
C       - linear), fits a B-spline approximant to the (X,Y) points
C       (in the L2 sense) and reports either
C
C       (a) the values of the smoothed piecewise-polynomial approximant or
C       (b) the derivative of the approximant
C
C       at the break points.
C       The resulting vectors are passed back to CCPLOT for direct plotting.
C
C       This USER_FUNCTION call the following subroutines from the
C       public-domain package BSPLINES
C
C               L2KNTS
C               L2APPR
C               BSPLPP
C               PPVALU
C               NEWNOT
C
C       Listings of these subroutines can be found in the book
C       Carl deBoor,    "A Practical Guide to Splines", Springer Verlag,
C                                                        New York, NY (1978)
C
C%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%

COMMON /USER_COM/ IP(10)
        REAL X(N),Y(N)
        INTEGER IOPT(4)
        TYPE 10
10      FORMAT('$Enter spline order: ')
        ACCEPT *,IOPT(1)
        IOPT(1)=IOPT(1)+1
        TYPE 20
20      FORMAT('$Enter number of break points: ')
```

```
        ACCEPT *,IOPT(2)
        TYPE 30
30      FORMAT('$Enter number of times to move breaks for optimization: ')
        ACCEPT *,IOPT(3)
        TYPE 40
40      FORMAT('$Function (0 = Smooth, 1= Derivative vs value): ')
        ACCEPT *,IOPT(4)
C
        do i=1,n
                x(i)=alog10(x(i))
        enddo
        CALL MYSMOOTH(X,Y,N,IOPT)
        do i=1,n
                x(i)=10**x(i)
        enddo
        RETURN
        END
C
C%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%
C
        SUBROUTINE MYSMOOTH(XV,YV,NV,IOPT)
C
C%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%
C
        REAL XV(NV),YV(NV)
        INTEGER IOPT(4)
        PARAMETER LPKMAX=100,NTMAX=500,LTKMAX=2000
        DIMENSION BCOEF(LPKMAX),Q(LTKMAX),SCRTCH(NTMAX),T(NTMAX)
        REAL BREAK(LPKMAX),COEF(LTKMAX)
        INTEGER L,K,NTAU
        REAL TAU(NTMAX),GTAU(NTMAX)
C
        NTAU=NV
        DO IK=1,NTAU
                TAU(IK)=XV(IK)
                GTAU(IK)=YV(IK)
        END DO

C---K = ORDER OF SPLINES + 1
C---L = NUMBER OF BREAK POINTS - 1

K=IOPT(1)
        L=IOPT(2)
        NTIMES=IOPT(3)
        ADDBRK=0.0

C---Calculate break points

STEP=(TAU(NTAU)-TAU(1))/L
        BREAK(1)=TAU(1)
        DO IK=2,L
                BREAK(IK)=BREAK(IK-1)+STEP
        END DO
        BREAK(L+1)=TAU(NTAU)

C---Calculate knots corresponding to break points

CALL L2KNTS(BREAK,L,K,T,N)
```

```
        LBEGIN=L
        NT=1

C---Call main subroutine that performs the L2 approximation 10      call L2APPR(T,N,K,Q,SCRTCH,BCOEF,TAU,GTAU,NTAU)

C---We have the L2 approximation
C---Get the piecewise-polynomial representation
C
        call BSPLPP(T,BCOEF,N,K,Q,BREAK,COEF,L)

C---Evaluate function and first derivative (i.e. rate)
C---at the break points
C
        IF(IOPT(4).EQ.1)GOTO 20                 !DERIVATIVE REQUIRED
        STEP=(TAU(NTAU)-TAU(1))/200.
        XV(1)=TAU(1)
        DO IK=2,200
                XV(IK)=XV(IK-1)+STEP
        END DO
        XV(201)=TAU(NTAU)
        IDERIVE=0
        IF(IOPT(4).EQ.2)IDERIVE=1
        DO LL=1,201
                YV(LL)=PPVALU(BREAK,COEF,L,K,XV(LL),IDERIVE)
        ENDDO
        NV=201
        GOTO 30
20      DO LL=1,NTAU
                YV(LL)=PPVALU(BREAK,COEF,L,K,TAU(LL),1)
                XV(LL)=PPVALU(BREAK,COEF,L,K,TAU(LL),0)
        ENDDO
30      IF (NT.GE.NTIMES)RETURN C---Move the knots around so that we can get a better approximation
C
        LNEW=LBEGIN+FLOAT(NT)*ADDBRK
        CALL NEWNOT(BREAK,COEF,L,K,SCRTCH,LNEW,T)
        CALL L2KNTS(SCRTCH,LNEW,K,T,N)

NT=NT+1
        GO TO 10
        END
C
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%%%
```

CLIO$DUB4:[CONTROL.TOOLKIT]IOD.FOR

```fortran
C%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%
C
C        PROGRAM IOD
C
C%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%*
C
C        COPYRIGHT (c) 1989 by Kyriacos Zygourakis
C        ALL RIGHTS RESERVED
C
C        Written by Kyriacos Zygourakis
C
C        This program calls the following subroutines from the
C        ICOMETRICS WINDOW Library (COPYRIGHT (C) 1987,1988,1989 by
C        Rush R. Record, Everest Technologies)
C
C             MAP_GREYSCALE
C             BIGMOVE
C             COPY_BITMAP
C
C%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%
C
C        This program performs integrated optical density (IOD)
C        calculations from digitized grey scale images
C        A bitmap image (of the same size) may be specified as a "MASK"
C        in order to exclude specific areas of the grey scale image from
C        the calculations
C
C%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%

IMPLICIT INTEGER*4 (A-Z)
         INCLUDE '$disk1:[rhr.window]IMAGE.PAR'

BYTE BYTEMAP(2048*2048)
         LOGICAL*1 X(2048*2048)
         CHARACTER*80 GREYSCALE,BITFILE,OUTFILE
         INTEGER*4 COUNT(0:255), TOTPIX, OUTLO, OUTHI
         REAL*4 A(0:255),H(0:255),GRAY_LEVEL,HD,DIFF,CUM
         REAL*4 IOD,MGL,VARIANCE,ENERGY,SKEWNESS
         REAL*4 SIZX,SIZY
C
         STRUCTURE/IMAGE/
               INTEGER*4 TYPE
               INTEGER*4 NBPR
               INTEGER*4 NROW
               REAL*4    SIZX
               REAL*4    SIZY
               INTEGER*2 XUNITS,YUNITS
               INTEGER*4 DIGITIM(2)
               CHARACTER*32 NAME
               BYTE %FILL(512-64)
         END STRUCTURE
```

```
          RECORD/IMAGE/H
          COMMON/HEAD/ H

C---Get greyscale image name

WRITE(6,*) ' '
          CALL LIB$GET_INPUT(GREYSCALE,'Greyscale image ? ',LENGREY)
          IF(LENGREY.GT.0) THEN
                  INDOT=INDEX(GREYSCALE,'.')
                  IF(INDOT.EQ.0) THEN
                          GREYSCALE=GREYSCALE(1:LENGREY)//'.N'
                          OUTFILE=GREYSCALE(1:LENGREY)//'.ODAT'
                          LENGREY=LENGREY+2
                  ELSE
                          OUTFILE=GREYSCALE(1:INDOT-1)//'.ODAT'

ENDIF
          ENDIF

C---Get info on greyscale image

CALL READ_HEADER(GREYSCALE,IERR)
          IF(IERR.EQ.64) THEN
                  WRITE(6,910) GREYSCALE(1:LENGREY)
                  STOP 'ABORT'
          ENDIF
          IF(IERR.EQ.128) THEN
                  WRITE(6,911) GREYSCALE(1:LENGREY)
                  STOP 'ABORT'
          ENDIF
          IF( H.TYPE .NE. 1) THEN
                  WRITE(6,920) GREYSCALE(1:LENGREY)
                  STOP 'ABORT'
          ENDIF

C---Open output file. On exit this file will contain the
C---optical density histogram and measurements

OPEN(UNIT=116,FILE=OUTFILE,STATUS='NEW')
          WRITE(116,901) GREYSCALE

901       FORMAT( ' Optical density data for image ',A/)

C---Get "mask" bitmap name
C---Areas specified by this bitmap will be excluded from
C---subsequent calculations CALL LIB$GET_INPUT(BITFILE,'Punch-out bitmap     ? ',LENFIL)
          INDOT=INDEX(BITFILE,'.')
          IF(INDOT.EQ.0) THEN
                  BITFILE=BITFILE(1:LENFIL)//'.O'
                  LENFIL=LENFIL+2
          ENDIF
          WRITE(116,902) BITFILE
902       FORMAT( ' Punch-out bitmap : ',A/)

C---Read mask bitmap

CALL OTX(BITFILE, LENFIL, NPX, NPY, X)

C---Map greyscale image
```

```
            STATUS=MAP_GREYSCALE(GREYSCALE,NBPR,NROW,SIZX,SIZY,IXU,IYU,IADR,.TRUE.)
            IF(NBPR.NE.NPX) STOP 'ABORT - NBPR IS NOT EQUAL TO NPX'
            IF(NROW.NE.NPY) STOP 'ABORT - NROW IS NOT EQUAL TO NPY'
            CALL BIGMOVE(NBPR*NROW,%VAL(IADR),BYTEMAP)

C---Select pixels according to punch-out bitmap

DO J=1,NROW
                DO I=1,NBPR
                    IND=(J-1)*NBPR+I
                    M=ZEXT(BYTEMAP(IND))
                    IF(X(IND)) COUNT(M)=COUNT(M)+1
                    IF(M.LT.16) OUTLO=OUTLO+1
                    IF(M.GT.239) OUTHI=OUTHI+1
                ENDDO
            ENDDO

C---TOTPIX is the total number of selected pixels

TOTPIX=0
            DO K=16,239
                TOTPIX=TOTPIX+COUNT(K)
            ENDDO
            IF(TOTPIX.EQ.0) THEN
                WRITE(116,*) 'No pixels selected !'
                CALL EXIT
            ENDIF
            WRITE(116,930) NBPR,NROW,NBPR*NROW,TOTPIX
            IF(TOTPIX.NE.NBPR*NROW) WRITE(116,935) OUTLO,OUTHI C---Area function A(D) : number of pixels having gray level .GE. D
C---Histogram       H(D) : - dA(D)/dD    (pdf)
C---Integrated optical density IOD = SUM [ k H(k) ] for k=16,239
C---Mean Gray Level             MGL = IOD / SUM[ H(k) ] for k=16,239

C---Calculate integrated optical density IOD

IOD=0.0
            DO I=16,239
                GRAY_LEVEL=(FLOAT(I)-16.0)/223.
                IOD=IOD+GRAY_LEVEL*FLOAT(COUNT(I))
            ENDDO
            MGL=IOD/FLOAT(TOTPIX)

VARIANCE=0.0
            ENERGY=0.0
            SKEWNESS=0.0
            DO I=16,239
                GRAY_LEVEL=(FLOAT(I)-16.0)/223.
                HD=FLOAT(COUNT(I))/FLOAT(TOTPIX)
                DIFF=(GRAY_LEVEL-MGL)
                VARIANCE=VARIANCE+DIFF*DIFF*HD
                ENERGY=ENERGY+HD*HD
                SKEWNESS=SKEWNESS+DIFF*DIFF*DIFF*HD
            ENDDO
            SKEWNESS=SKEWNESS/(VARIANCE**1.5)

WRITE(116,940) MGL,VARIANCE,ENERGY,SKEWNESS
```

```
                CUM=0.0
                DO K=16,239
                        GRAY_LEVEL=(FLOAT(K)-16.0)/223.
                        HD=FLOAT(COUNT(K))/FLOAT(TOTPIX)
                        CUM=CUM+HD
                        WRITE(116,942) GRAY_LEVEL,COUNT(K),HD,CUM
                ENDDO

910     FORMAT( ' ERROR - Cannot open file ',a)
911     FORMAT( ' ERROR - Cannot read the header of ',a)
920     FORMAT( ' ERROR - File ',a,' is not a greyscale image')
930     FORMAT( ' Image size : ',i4,'x',i4,' ( ',i8,' bytes)',/,
       1        ' Byte count = ',I8/)
935     FORMAT( ' LOW BYTES  = ',I8,'   HIGH BYTES : ',I8/)
940     FORMAT( ' Mean optical density = ',F8.5,/,
       1        ' Variance  = ',F8.5,/,
       2        ' Energy    = ',F8.5,/,
       3        ' Skewness  = ',F8.5/)
942     FORMAT(1X,F8.5,2X,I8,2X,G12.5,2X,F8.5)

END
C
C%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%
C
        SUBROUTINE READ_HEADER(FILE,IERR)
C
C%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%
C
        CHARACTER*80 FILE
        CHARACTER*1  HEADER(512)
        COMMON/HEAD/ HEADER

C---Read image file header

OPEN(UNIT=103, FILE=FILE, ERR=100, STATUS='OLD', FORM='UNFORMATTED')
        READ(103,ERR=200) (HEADER(I), I=1,512)

CLOSE(103)
        IERR=0
        RETURN
C
100     IERR=64
        RETURN
C
200     IERR=128
        RETURN
        END
C
C%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%
C
        SUBROUTINE OTX(FILE, LENFIL, NPX, NPY, X)
C
C%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%
```

```fortran
C
      PARAMETER (NXDIM=2048)
      PARAMETER (NYDIM=2048)
      PARAMETER (NBDIM=NXDIM*NYDIM/8)
      LOGICAL*1 X(NXDIM*NYDIM)
C
      BYTE ATRAN(0:255)
      BYTE BITDATA(NBDIM)
      CHARACTER BUF*64
      CHARACTER*132 RECORD
      COMMON/BITS/BITDATA LOGICAL RLE
      CHARACTER*80 FILE
      CHARACTER*12 TEMPORA
      INTEGER*4 LENFIL
      INTEGER*4 NPX, NPY, IUNX, IUNY, IXO, IYO
      REAL*4 SPX, SPY
      DATA TEMPORA/'ELR_BITMAP.O'/

STRUCTURE/IMAGE/
              INTEGER*4 TYPE
              INTEGER*4 NBPR
              INTEGER*4 NROW
              REAL*4    SIZX
              REAL*4    SIZY
              INTEGER*2 XUNITS,YUNITS
              INTEGER*4 DIGITIM(2)
              CHARACTER*32 NAME
              BYTE %FILL(512-64)
      END STRUCTURE
      RECORD/IMAGE/H
      COMMON/HEAD/ H

C---Load translation table for bit inversion

DO J=0,255
              K=J
              M = 0
              DO L=1,8

M=2*M
                      IF(K) M=M+1
                      K=K/2
              ENDDO
              ATRAN(J) = M
      ENDDO

C---Let's see the bitmap now
C---Get info from file header

CALL READ_HEADER(FILE,IERR)
      IF(IERR.EQ.64) THEN
              WRITE(6,910) FILE(1:LENFIL)
              STOP 'ABORT'
      ENDIF
      IF(IERR.EQ.128) THEN
              WRITE(6,911) FILE(1:LENFIL)
              STOP 'ABORT'
      ENDIF
910   FORMAT( ' ERROR - Cannot open file ',a)
```

```
911     FORMAT( ' ERROR - Cannot read the header of ',a)

C---Process info from header

RLE=.FALSE.
        IF( H.TYPE .NE. 0) THEN
                IF(H.TYPE.EQ.2) THEN
                        RLE=.TRUE.
                        CALL COPY_BITMAP(FILE(1:LENFIL),TEMPORA(1:12))
                ELSE
                        WRITE(6,920) FILE(1:LENFIL)
920                     FORMAT( ' ERROR - File ',a,' is not a bitmap')
                        STOP 'ABORT'
                ENDIF
        ENDIF C---Sizes and units NPX = H.NBPR
        NPY = H.NROW
        SPX = H.SIZX
        SPY = H.SIZY
        IUNX = H.XUNITS
        IUNY = H.YUNITS C---Check size NBX = NPX/8
        IF(8*NBX .NE. NPX) THEN
                WRITE(6,930) FILE(1:LENFIL), NPX
930             FORMAT(/' ERROR - Bitmap ',A,
     1                  ' has nonconforming width (NBPR=',i4,')')
                STOP 'ABORT'
        ENDIF C---Read bitmap IF(RLE) THEN
                OPEN(UNIT=71, FILE=TEMPORA, STATUS='OLD', FORM='UNFORMATTED')
        ELSE OPEN(UNIT=71, FILE=FILE, STATUS='OLD', FORM='UNFORMATTED')
        ENDIF
        CALL BITLOAD(NPX,NPY)
        IF(RLE) THEN
                CLOSE(71,DISP='DELETE')
        ELSE
                CLOSE(71)
        ENDIF C---Fill X array

N_BYTE_X = NPX/8

DO J = 1,NPY

C-------One line at a time

LINE = (J-1)*N_BYTE_X
                DO K = 1,N_BYTE_X
```

```
C-------Get byte and invert bits

M = ZEXT(ATRAN(ZEXT(BITDATA(LINE+K))))
                        JOFFSET=8*(LINE+K-1)

C-------and unpack it

DO JJ=1,8
                                KCOM=2**(8-JJ)
                                IF(M.GE.KCOM) THEN
                                        X(JOFFSET+JJ)=1
                                        M=M-KCOM
                                ENDIF
                        ENDDO
                ENDDO

ENDDO
C
        RETURN
        END
C
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%%%
C
        SUBROUTINE BITLOAD (NPX, NPY)
C
C%%%%%%%%%%%%%%%%%%%%%%%%%%%%%%%%%%%%%%%%%%%%%%%%%%%%%%%%%%%%%%%%%%%%
C%%%%%%%%%%%%%%%%%%%%%%%%%%%%%%%%%%%%%%%%%%%%%%%%%%%%%%%%%%%%%%%%%%%%
C
        PARAMETER (NXDIM=512)
        PARAMETER (NYDIM=512)
        PARAMETER (NBDIM=NXDIM*NYDIM/8)
C
        BYTE BITMAP(NBDIM)
        BYTE BUFFER(512)
        COMMON/BITS/BITMAP
C
C               Read header for O file C
        READ(71) (BUFFER(I), I=1, 512)
C
C               Now read the O file
C
        NBYTE = NPX*NPY/8
        NREC  = NBYTE/512
        DO J=1, NREC
                IKK = (J-1)*512
                READ(71) (BUFFER(I), I=1,512)
                DO L=1,512
                        KOUNT = IKK+L
                        BITMAP(KOUNT) = BUFFER(L)
                ENDDO
        ENDDO
C
C               Read possible remainder from last record
C
        NREST = 0
        IF(NREC*512 .NE. NBYTE) THEN
```

```
              NREST = NBYTE - 512*NREC
              READ(71) (BUFFER(I), I=1,NREST)
              DO L=1,NREST
                   BITMAP(KOUNT+L) = BUFFER(L)
                   ENDDO
         ENDIF
C
         RETURN
         END
```

What is claimed is:

1. A method of characterizing the structure of cells and aggregates of cells in a cell suspension, including the steps of:

incubating a cell suspension and reagent to produce non-aggregated cells and aggregates of cells;

producing at least one image of said non-aggregate cells and aggregates of cells;

characterizing an extent of aggregation of said cell suspension according to a ratio of a total area of said at least one image covered by sells and cell aggregates to total area of said at least one image covered by non-aggregated cells before aggregation begins.

2. The method of claim 1, wherein said producing step comprises producing a time sequence of multiple images of said aggregates of cells, and wherein said characterizing step comprises characterizing a structure of said aggregates of cells according to a time rate of change of the said shape factor distribution.

3. The method of claim 1, wherein said incubating step includes creating a uniform cell distribution on a bottom of an inverted frusto-conical tapered well.

4. The method of claim 3, wherein said producing step comprises:

producing quadrant images of said aggregates of cells in four quadrants of said well; and combining said quadrant images to form a single image of said aggregates of cells.

5. A method of characterizing lymphocyte function in a cell suspension, including the steps of:

incubating a cell suspension to produce aggregates of cells;

producing at least one image of said aggregates of cells;

adding to said cell suspension monoclonal antibodies to cell surface molecules;

producing at least one image of said aggregates of cells after adding said monoclonal antibodies; and characterizing lymphocyte function in said cell suspension according to the variations resulting from adding said monoclonal antibodies in a size distribution, s(A)dA, of said aggregates of cells, wherein s(a)dA is a fraction of total area of each said at least one image covered by aggregates of cells attributable to aggregates having an area between A and A+dA.

6. A method of characterizing lymphocyte function in a cell suspension, including the steps of:

incubating a cell suspension to produce aggregates of cells;

producing at least one image of said aggregates of cells;

changing at least one chemical, physical, or biological condition of said aggregates of cells;

producing at least one image of said aggregates of cells after said condition has been changed; and characterizing lymphocyte function in said cell suspension according to the variations resulting from said changed condition in a shape factor distribution, s(τ)d(τ), wherein s(τ)d(τ) is a fraction of a total area of said at least one image covered by aggregates attributable to aggregates having a shape factor between τ and τ+d(τ), and wherein:

$$\tau = \frac{P^2}{4\pi A}$$

P being a perimeter of an aggregate of cells, and A being an area of said aggregate of cells.

7. The method of claim 6, wherein said changing step includes adding to said cell suspension monoclonal antibodies to cell surface molecules.

8. The method of claim 6, wherein said incubating step comprises incubating a cell suspension and a reagent, and wherein said changing step includes adding at least one additional reagent.

9. A method of characterizing the structure of cells and aggregates of cells in a cell suspension, comprising the steps of:

incubating a cell suspension and reagent to produce a mixture of non-aggregated cells and aggregates of cells;

producing a time sequence of images of said mixture of non-aggregated cells and aggregates of cells; and characterizing a structure of said non-aggregated cells and aggregates of cells according to a time rate of change of a size distribution, s(A)dA, of said non-aggregated cells and aggregates of cells, wherein s(A)dA is a fraction of total area of each image of said time sequence of images covered by non-aggregated cells and aggregates of cells attributable to non-aggregated cells and aggregates of cells having an area between A and A+dA.

10. A method of characterizing the structure of cells and aggregates of cells in a cell suspension, comprising the steps of:

incubating a cell suspension and reagent to produce a mixture of non-aggregated cells and aggregates of cells;

producing quadrant images of said non-aggregated cells and aggregates of cells in four quadrants, and combining said quadrant images to form a single image of said non-aggregated cells and aggregates of cells; and characterizing a structure of said non-aggregated cells and aggregates of cells according to a size distribution, s(A)dA, of said non-aggregated cells and aggregates of cells, wherein s(A)dA is a fraction of total area of said single image covered by non-aggregated cells and aggregates of cells attributable to non-aggregated cells and aggregates of cells having an area between A and A+dA.

11. A method of characterizing a structure of cells and aggregates of cells in a cell suspension, comprising the steps of:

incubating a cell suspension and reagent to produce a mixture of non-aggregated cells and aggregates of cells;

producing a time sequence of images of said non-aggregated cells and aggregates of cells; and characterizing an extent of aggregation of said cell suspension according to a time rate of change of a ratio of total area of each image of said sequence of images covered by non-aggregated cells and aggregates of cells to total area of each image.

12. A method of characterizing lymphocyte function in a cell suspension, including the steps of:

incubating a cell suspension to produce aggregates of cells; producing at least one image of said aggregates of cells;

adding to said cell suspension monoclonal antibodies to cell surface molecules;

producing at least one image of said aggregates of cells after adding of said monoclonal antibodies; and characterizing lymphocyte function in said cell suspension according to variations resulting from adding of said monoclonal antibodies in a ratio of a total area of said at least one image covered by cell aggregates to total area of said at least one image.

* * * * *

UNITED STATES PATENT AND TRADEMARK OFFICE
CERTIFICATE OF CORRECTION

PATENT NO. : 5,487,112

DATED : January 23, 1996

INVENTOR(S) : Kyriacos Zygourakis *et al.*

It is certified that error appears in the above-indentified patent and that said Letters Patent is hereby corrected as shown below:

In column 43, lines 2-13, delete claim 1 in its entirety, and substitute therefor:

--1. A method of characterizing the structure of aggregates of cells in a cell suspension, including the steps of:
    incubating a cell suspension and reagent to produce aggregates of cells:
    producing at least one image of said aggregates of cells;
    characterizing a structure of said aggregates of cells according to a shape factor distribution $s(\tau)d(\tau)$, wherein $s(\tau)d(\tau)$ is a fraction of a total area of said at least one image covered by aggregates attributable to aggregates having a shape factor between $\tau$ and $\tau+d(\tau)$, and wherein:

$$\tau = \frac{p^2}{4\pi A}$$

p being a perimeter of an aggregate of cells, and A being an area of said aggregate of cells.--

Signed and Sealed this

Twenty-second Day of October, 1996

Attest:

BRUCE LEHMAN

*Attesting Officer*     *Commissioner of Patents and Trademarks*